(12) United States Patent
Mahadevan et al.

(10) Patent No.: US 10,507,294 B2
(45) Date of Patent: Dec. 17, 2019

(54) HANDHELD DYSPNEA TREATMENT DEVICE WITH DRUG AND GAS DELIVERY

(71) Applicant: KONINKLIJKE PHILIPS N.V., Eindhoven (NL)

(72) Inventors: Anandi Mahadevan, Murrysville, PA (US); Elias George Diacopoulso, Export, PA (US)

(73) Assignee: Koninklijke Philips N.V., Eindhoven (NL)

( * ) Notice: Subject to any disclaimer, the term of this patent is extended or adjusted under 35 U.S.C. 154(b) by 1236 days.

(21) Appl. No.: 14/420,151

(22) PCT Filed: Jul. 30, 2013

(86) PCT No.: PCT/IB2013/056247
§ 371 (c)(1),
(2) Date: Feb. 6, 2015

(87) PCT Pub. No.: WO2014/027267
PCT Pub. Date: Feb. 20, 2014

(65) Prior Publication Data
US 2015/0283339 A1 Oct. 8, 2015

Related U.S. Application Data

(60) Provisional application No. 61/682,398, filed on Aug. 13, 2012.

(51) Int. Cl.
*A61M 15/00* (2006.01)
*A61M 16/00* (2006.01)
(Continued)

(52) U.S. Cl.
CPC .......... *A61M 15/002* (2014.02); *A61M 11/00* (2013.01); *A61M 15/00* (2013.01);
(Continued)

(58) Field of Classification Search
CPC ...... A61M 11/00; A61M 13/00; A61M 15/00; A61M 15/0001; A61M 15/002;
(Continued)

(56) References Cited

U.S. PATENT DOCUMENTS 5,363,842 A 11/1994 Mishelevich
6,012,450 A * 1/2000 Rubsamen ........ A61M 15/0045
128/200.14

(Continued)

FOREIGN PATENT DOCUMENTS

| CN | 101193676 A | 6/2008 |
|---|---|---|
| CN | 101217993 A | 7/2008 |
| WO | WO0149349 A1 | 7/2001 |

*Primary Examiner* — Colin W Stuart
(74) *Attorney, Agent, or Firm* — Michael W. Haas

(57) ABSTRACT

A portable handheld pressure support system configured to provide rapid recovery from dyspnea of a subject is provided. The pressure support system is configured to be small and lightweight so that the subject carries the system and use the system as needed without requiring a device to be worn on the face. The system includes one or more of a pressure generator, a subject interface, a medicament inlet port, one or more sensors, one or more valves, one or more processors, a user interface, electronic storage, a portable power source, a housing, a handle, and/or other components.

15 Claims, 4 Drawing Sheets

(51) Int. Cl.

| | | |
|---|---|---|
| *A61M 11/00* | (2006.01) | |
| *A61M 16/12* | (2006.01) | |
| *A61M 16/14* | (2006.01) | |
| *A61M 16/20* | (2006.01) | |
| *A61M 16/06* | (2006.01) | |
| *A61M 16/10* | (2006.01) | |

(52) U.S. Cl.
CPC ...... *A61M 15/0001* (2014.02); *A61M 15/009* (2013.01); *A61M 15/0065* (2013.01); *A61M 15/0066* (2014.02); *A61M 15/0091* (2013.01); *A61M 16/0003* (2014.02); *A61M 16/0057* (2013.01); *A61M 16/021* (2017.08); *A61M 16/022* (2017.08); *A61M 16/024* (2017.08); *A61M 16/06* (2013.01); *A61M 16/12* (2013.01); *A61M 16/14* (2013.01); *A61M 16/202* (2014.02); *A61M 16/0006* (2014.02); *A61M 16/107* (2014.02); *A61M 16/1055* (2013.01); *A61M 2016/0018* (2013.01); *A61M 2016/0021* (2013.01); *A61M 2205/332* (2013.01); *A61M 2205/3334* (2013.01); *A61M 2205/3375* (2013.01); *A61M 2205/3553* (2013.01); *A61M 2205/3592* (2013.01); *A61M 2205/502* (2013.01); *A61M 2205/505* (2013.01); *A61M 2205/52* (2013.01); *A61M 2205/581* (2013.01); *A61M 2205/582* (2013.01); *A61M 2205/583* (2013.01); *A61M 2205/82* (2013.01); *A61M 2205/8206* (2013.01); *A61M 2205/8237* (2013.01); *A61M 2205/8262* (2013.01); *A61M 2230/63* (2013.01)

(58) Field of Classification Search
CPC .......... A61M 15/0021; A61M 15/0065; A61M 15/0066; A61M 15/009; A61M 15/0091; A61M 16/024; A61M 16/12; A61M 16/14; A61M 16/0003; A61M 16/202; A61M 16/0057; A61M 16/022; A61M 16/021; A61M 2016/0018; A61M 2205/3334; A61M 2205/82; A61M 2205/8206
USPC ............. 128/203.12, 203.15, 204.17, 204.18
See application file for complete search history.

(56) References Cited

U.S. PATENT DOCUMENTS

| | | |
|---|---|---|
| 2002/0104541 A1 | 8/2002 | Bibi |
| 2003/0140921 A1* | 7/2003 | Smith ................ A61J 1/065 128/200.14 |
| 2004/0223917 A1 | 11/2004 | Hindle |
| 2004/0249300 A1 | 12/2004 | Miller |
| 2005/0051168 A1 | 3/2005 | DeVries |
| 2006/0243275 A1 | 11/2006 | Ruckdeschel |
| 2008/0066739 A1* | 3/2008 | LeMahieu ........... A61M 11/041 128/200.14 |
| 2008/0264417 A1 | 10/2008 | Manigel |
| 2009/0025714 A1* | 1/2009 | Denyer ................ A61M 15/00 128/200.23 |
| 2009/0126734 A1 | 5/2009 | Dunsmore |
| 2009/0199852 A1 | 8/2009 | McIntyre |
| 2012/0097155 A1 | 4/2012 | Iyer |
| 2012/0167878 A1 | 7/2012 | Belson |

* cited by examiner

HANDHELD DYSPNEA TREATMENT DEVICE WITH DRUG AND GAS DELIVERY

CROSS-REFERENCE TO RELATED APPLICATIONS

This patent application claims the priority benefit under 35 U.S.C. § 371 of international patent application no. PCT/IB2013/056247, filed Jul. 30, 2013, which claims the priority benefit under 35 U.S.C. § 119(e) of U.S. Provisional Application No. 61/682,398 filed on Aug. 13, 2012, the contents of which are herein incorporated by reference.

BACKGROUND OF THE INVENTION

1. Field of the Invention

The present disclosure pertains to a portable handheld pressure support system configured to provide relief and/or recovery from dyspnea.

2. Description of the Related Art

It is well known to apply a positive air pressure (PAP) to a patient's airway to keep the airway open and avoid collapse during breathing. This positive pressure effectively "splints" the airway, thereby maintaining an open passage to the lungs. Dyspnea, or shortness of breath, is a primary symptom of chronic obstructive pulmonary disease (COPD). COPD patients may suffer occurrences of dyspnea when exerting themselves. The forms of exertion may include performing household chores, walking to the local store, or climbing a set of stairs. An onset of dyspnea limits a patient's ability to perform activities and can trigger apprehension or panic, further reducing the patient's ability to function. Many COPD patients require oxygen when exerting themselves and/or during sleep. COPD patients carry short acting bronchodilators to alleviate their symptoms of dyspnea. Bronchodilators have drawbacks including that they are steroid based, and are slow acting (4-20 minutes).

SUMMARY OF THE INVENTION

Accordingly, it is an object of one or more embodiments of the present invention to provide a handheld pressure support system with supplemental oxygen and drug delivery capability configured to provide recovery from dyspnea of a subject. This combination will provide the patients the instant relief using PAP therapy and long lasting relief using drug delivery in an appropriate manner. The supplemental O2 will help the patient to not desaturate. The pressure support system includes a pressure generator configured to generate a pressurized flow of breathable gas for delivery to an airway of the subject, a subject interface configured to communicate the pressurized flow of breathable gas to the airway of the subject, one or more sensors configured to generate output signals conveying information related to one or more gas parameters of the pressurized flow of breathable gas, a medicament inlet port configured to couple to a supply that includes medicament, one or more valves configured to selectively control a flow including medicament through the medicament inlet port, one or more processors configured to execute computer program modules, a portable power source, a housing configured to contain the system, and a handle attached to and/or formed by the housing configured to be grasped by the subject to hold the housing in position with respect to the airway of the subject as the pressurized flow of breathable gas is delivered to the airway of the subject. The computer program modules comprises a generator control module configured to control operation of the pressure generator to generate the pressurized flow of breathable gas based on the output signals from the one or more sensors, a medicament module configured to obtain a flow including medicament for inhalation by the subject, and a valve control module configured to control the one or more valves in order to release the obtained flow including medicament into the pressurized flow of breathable gas for inhalation by the subject.

It is yet another aspect of one or more embodiments of the present invention to provide a method of providing recovery from dyspnea of a subject having an airway. The method, being implemented using a handheld pressure support system that includes a housing that includes a pressure generator, a subject interface, one or more sensors, a medicament inlet port, one or more valves, one or more processors, and a power source, comprises generating a pressurized flow of breathable gas by the pressure generator; communicating the pressurized flow of breathable gas to the airway of the subject with the subject interface; generating output signals conveying information related to one or more gas parameters of the pressurized flow of breathable gas by the one or more sensors; coupling the housing to a supply that includes medicament; selectively controlling a flow including medicament through the medicament inlet port; controlling generation of the pressurized flow of breathable gas based on the output signals from the one or more sensors; obtaining a flow including medicament for inhalation by the subject; controlling the one or more valves in order to release the obtained flow of medicament into the pressurized flow of breathable gas for inhalation by the subject; and portably powering the pressure generator, the one or more sensors, the one or more valves, and the one or more processors.

It is yet another aspect of one or more embodiments to provide a handheld pressure support system configured to provide recovery from dyspnea of a subject. The system comprises generating means for generating the pressurized flow of breathable gas; means for communicating the pressurized flow of breathable gas to the airway of the subject; sensing means for generating output signals conveying information related to one or more gas parameters of the pressurized flow of breathable gas; coupling means for coupling to a supply including medicament; first means for selectively controlling a flow including medicament through the coupling means; means for controlling the generating means based on the output signals, in accordance with a positive pressure support therapy regime; means for obtaining the flow including medicament for inhalation by the subject; control means for controlling the first means in order to release the obtained flow including medicament into the pressurized flow of breathable gas for inhalation by the subject; power means for portably powering the generating means, the sensing means, and the first means; housing means for containing the generating means, the sensing means, the first means, and the power means; and means for engaging a hand of the subject to be grasped by the subject to hold the housing means in position with respect to the airway of the subject, the means for engaging being connected to and/or formed by the housing means.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
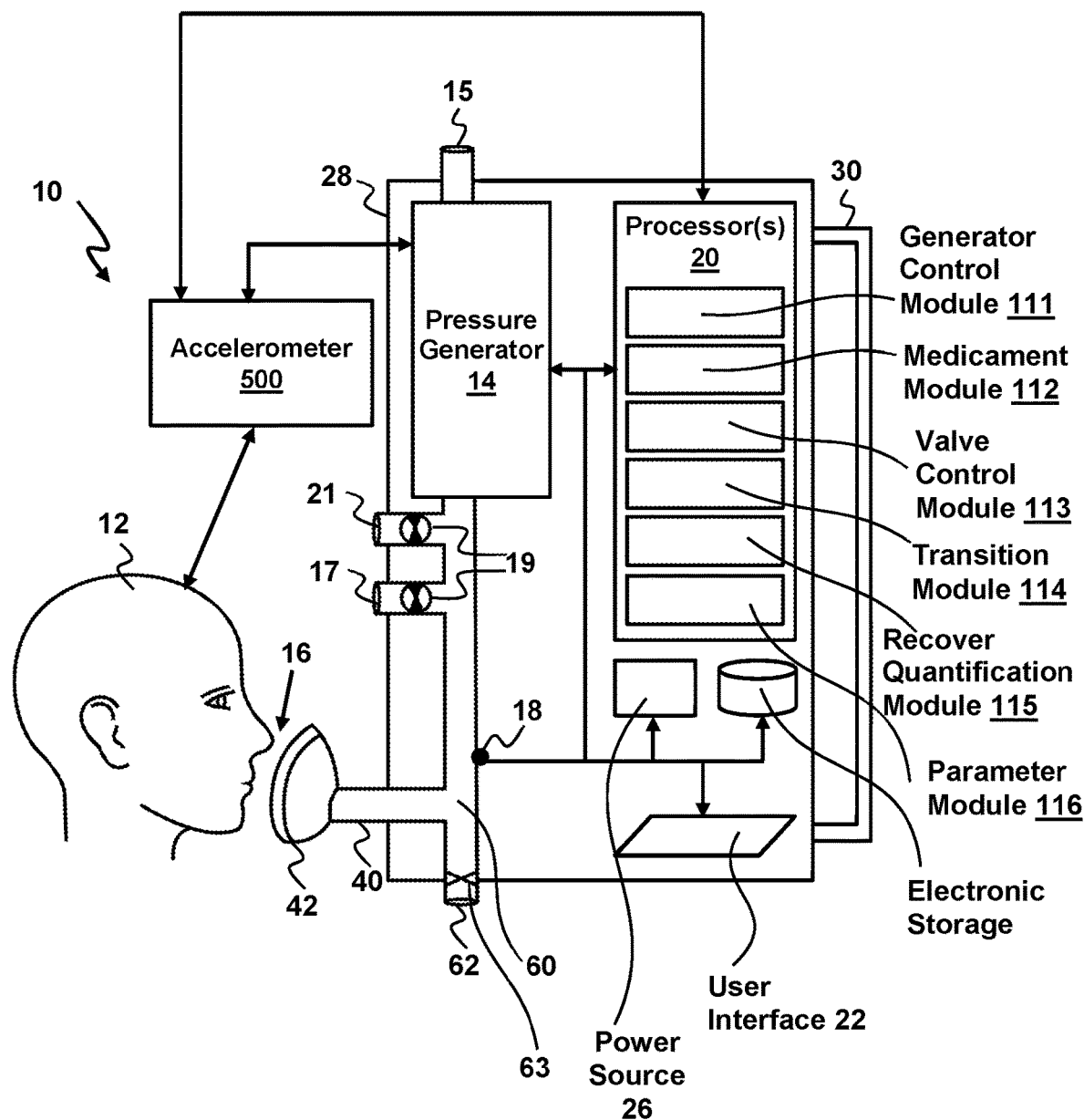
FIG. 1 illustrates a schematic of a portable handheld pressure support system configured to provide relief and/or recovery from dyspnea.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As used herein, the statement that two or more parts or components "engage" one another shall mean that the parts exert a force against one another either directly or through one or more intermediate parts or components. As used herein, the term "number" shall mean one or an integer greater than one (i.e., a plurality). As used herein, the term "include" shall be used inclusively to mean any item of a list, by example and without limitation, and/or any combination of items in that list, to the extent possible.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a portable handheld pressure support system 10 configured to provide relief and/or recovery from dyspnea of a subject 12. As used in this disclosure, the term "recovery" may be interpreted to include partial or complete recovery and/or partial or complete relief. Pressure support system 10 may interchangeably be referred to as system 10 herein. System 10 is configured to provide (optionally blending-gas-enriched) pressure support therapy including a pressurized flow of breathable gas that is delivered to the airway of the subject, and/or a flow including medicament. System 10 may be configured to treat COPD and/or other patients suffering from dyspnea and/or other conditions.

The pressure support therapy provided to dyspnea patients is configured to be used as needed by subject 12 to rapidly alleviate shortness of breath. System 10 is configured to be small and lightweight so that subject 12 may carry system 10 and use system 10 as needed without requiring a device to be worn on the face or other part of the body. The present disclosure contemplates that portable handheld pressure support system 10 may be used to treat symptoms and/or conditions related to dyspnea due to COPD, and/or for other uses. The other uses may include, for example, treating dyspnea related to pulmonary cancer, treating emphysema, treating pneumonia, treating Cheyne-Stokes respiration and/or other disordered breathing, improving the exercise capacity of any patient limited by dyspnea, preventative respiratory therapy, and/or other uses.

In some embodiments, system 10 comprises one or more of a pressure generator 14, an inlet 15, a subject interface 16, a blending gas inlet port 17, a medicament inlet port 21, one or more sensors 18, one or more valves 19, one or more processors 20 configured to execute various computer program modules, a user interface 22, electronic storage 24, a portable power source 26, a housing 28, a handle 30, and/or other components.

Pressure generator 14 is configured to generate a flow of gas for delivery to the airway of a subject 12. Pressure generator 14 may control one or more parameters of the flow of gas (e.g., flow rate, pressure, volume, temperature, gas composition, etc.) for therapeutic purposes, and/or for other purposes. By way of a non-limiting example, pressure generator 14 may be configured to control the flow rate and/or pressure of the flow of gas to provide pressure support to the airway of subject 12.

Pressure generator 14 receives a flow of gas from a gas source, e.g. ambient atmosphere, and elevates the pressure of that gas for delivery to the airway of subject 12. In some embodiments, pressure generator 14 receives a flow of gas from a gas source through an inlet or inlet port, such as inlet 15. Pressure generator 14 may include any device, such as, for example, a pump, blower, piston, or bellows, that is capable of elevating the pressure of the received flow of gas for delivery to a patient. Pressure generator 14 may include one or more valves for controlling the pressure and/or flow rate of delivered gas. The present disclosure also contemplates controlling the operating speed of the blower, either alone or in combination with such valves, to control the pressure and/or flow rate of gas provided to subject 12.

In some embodiments, pressure generator 14 may be configured to supply a pressurized flow of breathable gas at pressures up to about 40 cm-$H_2O$. In some embodiments, pressure generator 14 may be configured to supply a pressurized flow of breathable gas at pressures up to about 30 cm-$H_2O$. In some embodiments, pressure generator 14 may be configured to supply a pressurized flow of breathable gas at pressures up to about 20 cm-$H_2O$. In some embodiments, pressure generator 14 may be configured to supply a pressurized flow of breathable gas at pressures up to about 10 cm-$H_2O$.

Subject interface 16 is configured to communicate a flow of breathable gas, including the pressurized flow of breathable gas, to the airway of subject 12. In one embodiment, the breathable gas may include medicament. Subject interface 16 includes one or more of a conduit 40, an interface appliance 42, a filter (not shown in FIG. 1), and/or other components. In some embodiments, filter may be configured to filter one or more of pathogens, bacteria, particles, and/or materials. Conduit 40 is configured to convey the pressurized flow of gas to interface appliance 42. Interface appliance 42 is configured to deliver the flow of gas to the airway of subject 12. In some embodiments, interface appliance 42 is configured to be non-invasively engaged by the mouth of subject 12. Non-invasive engagement may comprise removably engaging one or more external orifices of the airway of subject 12 (e.g., nostrils and/or mouth) to communicate gas between the airway of subject 12 and interface appliance 42.

Interface appliance 42 may be removably coupled to conduit 40. Interface appliance 42 may be removed for cleaning and/or for other purposes. In some embodiments, conduit 40 is configured as a mouthpiece to be engaged by the mouth of subject 12.

Other (non-invasive) interface appliances may be configured as interface appliance 42. Some examples of non-invasive interface appliance 42 may include, a nasal cannula, a nasal mask, a nasal/oral mask, a full face mask, a total face mask, or other interface appliances that communicate a flow of gas with an airway of a subject. The present disclosure is not limited to these examples, and contemplates delivery of the flow of gas to the subject using any interface appliance. In some embodiments, system 10 may be connected to a classical respiratory circuit (e.g., a six-foot hose) such that the classical respiratory circuit functions as subject interface 16.

Medicament inlet port 21 is configured to couple system 10 to a supply that includes medicament. In some embodiments, such a supply may include breathable gas and/or other gas such that a supplied flow and/or volume of gas includes the medicament. Medicament inlet port 21 may couple housing 28 to a supply of medicament and/or a supply including medicament. In some embodiments, the coupling may comprise a removable attachment. In some embodiments, coupling may be accomplished through added plumbing and/or additional manufactured parts in order to provide the coupling to housing 28. In some embodiments, the supply including medicament may be contained in, for example, a canister, an inhaler containing aerosolized medication, a metered dose inhaler (MDI), nebulizer and/or another portable container separate from system 10. In these embodiments, the additional container may be portable, rechargeable, and/or replaceable. In some embodiments, the portable, rechargeable, and/or replaceable supply including medicament may be contained within system 10.

In some embodiments, medicament inlet port 21 may be fluidly coupled such that a supplied flow, including (or not including) medicament, is combined with the pressurized flow of breathable gas from pressure generator 14. Alternatively, and/or simultaneously, separate flows may be delivered in sequence and/or through separate flow paths.

Blending gas inlet port 17 is configured to couple system 10 to a supply of blending gas. In some embodiments the blending gas may comprise oxygen, and/or another gas, such as nitrogen, helium, heliox, etc. Blending gas inlet port 17 couples housing 28 to the supply of blending gas. In some embodiments, coupling may comprise a removable attachment. In some embodiments, coupling may be accomplished through added plumbing and/or additional manufactured parts to couple housing 28 to the supply of blending gas. In some embodiments, the supply of blending gas may be contained in, for example, a canister, an inhaler, and/or other portable container separate from system 10. In these embodiments, the additional container may be portable, rechargeable, and/or replaceable. In some embodiments, the portable, rechargeable, and/or replaceable supply of blending gas may be contained within system 10.

In some embodiments, blending gas inlet port 17 may be fluidly coupled such that a supplied flow including medicament is combined with one or both of the pressurized flow of breathable gas from pressure generator 14 and/or the flow including medicament from medicament inlet port 21. Alternatively, and/or simultaneously, separate flows may be delivered in sequence and/or through separate flow paths. In some embodiments, the functionality of blending gas inlet port 17 and medicament inlet port 21 as described herein may be implemented through one single joined inlet port.

One or more sensors 18 are configured to generate output signals conveying information related to one or more parameters of the gas within system 10 and/or the respiration of subject 12. The one or more parameters may include gas parameters related to the pressurized flow of breathable gas, breathing parameters related to respiration of subject 12, blending gas parameters related to the flow of blending gas through blending gas inlet port 17, parameters related to the flow including medicament through medicament inlet port 21, and/or other parameters. Sensors 18 may comprise one or more sensors that measure such parameters directly (e.g., through fluid communication with the flow of gas in interface appliance 42). Sensors 18 may comprise one or more sensors that generate output signals related to the one or more parameters indirectly. For example, sensors 18 may comprise one or more sensors configured to generate an output based on an operating parameter of pressure generator 14 (e.g., patient flow and/or pressure estimations from motor current, voltage, rotational velocity, and/or other operating parameters), as described in some more detail below.

The one or more gas parameters of the pressurized flow of breathable gas may comprise, for example, one or more of a flow rate, a volume, a pressure, humidity, temperature, acceleration, velocity, concentration of one or more constituents (e.g., the concentration of oxygen), and/or other gas parameters. Breathing parameters related to the respiration of subject 12 may comprise a tidal volume, a timing (e.g., beginning and/or end of inhalation, beginning and/or end of exhalation, etc.), a respiration rate, a duration (e.g., of inhalation, of exhalation, of a single breathing cycle, etc.), respiration frequency, a quantification of the level, type, and/or severity of dyspnea, a quantification of the progress towards recovery from (an occurrence of) dyspnea, and/or other breathing parameters. Gas parameters related to the flow through blending gas inlet port 17 and/or medicament inlet port 21 may comprise, for example, a gas pressure, a gas flow rate, a gas composition, and/or other gas parameters.

In some embodiments, one or more sensors 18 comprise one or more flow rate sensors configured to generate output signals conveying information related to the flow rate of the pressurized flow of breathable gas generated by pressure generator 14, the flow rate of the blending gas flowing through blending gas inlet 17, and/or the flow rate of the flow including medicament flowing through medicament inlet port 21. Flow rate sensors suitable for use as sensors 18 may include, for example, mechanical flow rate sensors, pressure based flow rate sensors, optical flow rate sensors, thermal mass flow rate sensors, magnetic flow rate sensors, and/or other flow rate sensors.

In some embodiments, one or more sensors 18 comprise one or more pressure sensors configured to generate output signals conveying information related to the pressure of the pressurized flow of breathable gas generated by pressure generator 14, the pressure of the blending gas flowing through blending gas inlet 17, and/or the pressure of the flow including medicament flowing through medicament inlet port 21. Pressure sensors suitable for use as sensors 18 may include, for example, mechanical sensors, capacitive sensors, electromagnetic sensors, piezoelectric sensors, optical sensors, and/or other pressure sensors.

In some embodiments, sensors 18 may comprise one or more oxygen sensors configured to generate output signals related to the concentration of oxygen in the pressurized flow of breathable gas delivered to subject 12.

Although sensors 18 are illustrated in FIG. 1 at a single location in system 10, this is not intended to be limiting. The one or more sensors 18 may include sensors disposed in a plurality of locations, such as for example, at various locations within (or in communication with) conduit 40, within pressure generator 14, within (or in communication with) interface appliance 42, within (or in communication with) blending gas inlet port 17, within (or in communication with) medicament inlet port 21, and/or other locations.

One or more valves 19 are configured to selectively control one or more of the flow of blending gas through blending gas inlet port 17, the flow including medicament through medicament inlet port 21, and/or the pressurized flow of breathable gas generated by pressure generator 14, and/or the delivery of any combination thereof to subject 12. In some embodiments the maximum flow rate through one or more valves 19 is about 30 liters per minute (lpm), about 20 lpm, about 10 lpm, about 8 lpm, about 6 lpm, about 4 lpm, and/or another maximum flow rate.

In some embodiments, one or more valves 19 may comprise one or more valves in series and/or in parallel. Examples of valves and/or other pressure regulating devices suitable for use as valve 19 include a plug valve, a ball valve, a check valve, a butterfly valve, a solenoid, a pressure switch, and/or other pressure regulating devices The pressure regulating devices mentioned above and/or other pressure regulating devices that may be used as valve 19 may be controlled magnetically, hydraulically, pneumatically, via an electric motor and/or another mode of control configured to open and/or close a valve and/or other pressure control device.

One or more processors 20 are configured to provide information processing capabilities in system 10. As such, processor(s) 20 may comprise one or more of a digital processor, an analog processor, a digital circuit designed to process information, an analog circuit designed to process information, and/or other mechanisms for electronically processing information. Although processor 20 is shown in FIG. 1 as a single entity, this is for illustrative purposes only. In some implementations, processor 20 may comprise a plurality of processing units. These processing units may be physically located within the same housing and/or device (e.g., housing 28 and/or pressure generator 14), or processor 20 may represent processing functionality of a plurality of devices operating in coordination.

As shown in FIG. 1, processor 20 is configured to execute one or more computer program modules. The one or more computer program modules may comprise one or more of a generator control module 111, a medicament module 112, a valve control module 113, a respiratory phase transition module 114, a recovery quantification module 115, a parameter module 116, and/or other modules. Processor 20 may be configured to execute modules 111-116 by software; hardware; firmware; some combination of software, hardware, and/or firmware; and/or other mechanisms for configuring processing capabilities on processor 20.

It should be appreciated that although modules 111-116 are illustrated in FIG. 1 as being co-located within a single processing unit, in implementations in which processor 20 comprises multiple processing units, one or more of modules 111-116 may be located remotely from the other modules. The description of the functionality provided by the different modules 111-116 described below is for illustrative purposes, and is not intended to be limiting, as any of modules 111-116 may provide more or less functionality than is described. For example, one or more of modules 111-116 may be eliminated, and some or all of its functionality may be provided by other modules 111-116. As another example, processor 20 may be configured to execute one or more additional modules that may perform some or all of the functionality attributed below to one of modules 111-116.

Parameter module 116 is configured to determine one or more parameters within system 10. The one or more parameters within system 10 may comprise gas parameters related to the pressurized flow of breathable gas, respiratory parameters, and/or other parameters. The one or more gas parameters of the pressurized flow of breathable gas may comprise, for example, one or more of a flow rate, a volume, a pressure, humidity, temperature, acceleration, velocity, and/or other gas parameters. Parameter module 116 is configured to determine the one or more parameters based on output signals of sensor(s) 18. The information determined by parameter module 116 may be used for controlling pressure generator 14, stored in electronic storage 24, and/or used by other computer program modules.

Respiratory phase transition module 114 is configured to determine respiratory phases (e.g., inhalation, exhalation) during breathing of subject 12. Respiratory phase transition module 114 may interchangeably be referred to as transition module 114 herein. The respiratory phase determinations made by module 114 are based on the output signals from sensors 18, information determined by parameter module 116, and/or other information. Transition module 114 may be configured to determine additional breathing parameters related to the respiration of subject 12. Additional breathing parameters related to the respiration of subject 12 may comprise a tidal volume, a timing (e.g., beginning and/or end of inhalation, beginning and/or end of exhalation, etc.), a respiration rate, a duration (e.g., of inhalation, of exhalation, of a single breathing cycle, etc.), respiration frequency, and/or other breathing parameters. The determinations made by transition module 114 may be used by, e.g., generator control module 111 and/or valve control module 113 to control pressure generator 14 to control the pressurized flow of breathable gas delivered to subject 12, may be stored in electronic storage 24, and/or used elsewhere within system 10. In some embodiments, transition module 114 is configured to determine the respiratory phase (e.g., inhalation, exhalation) based on changes in pressure, flow rate, other parameters determined by parameter module 116, and/or other information.

Generator control module 111 is configured to control pressure generator 14 to generate a flow of (pressurized) gas in accordance with a (positive airway) pressure support therapy regime. In pressure support therapy the pressurized flow of gas generated by pressure generator 14 may be controlled to replace, aid, and/or compliment a patient's regular breathing. Pressure support therapy may be used to maintain an open airway in a patient so that oxygen and carbon dioxide may be exchanged more easily, requiring little and/or no effort from the patient. By way of non-limiting example, generator control module 111 may control pressure generator 14 such that the pressure support provided to the subject via the flow of gas comprises continuous positive airway pressure support (CPAP), bi-level positive airway pressure support (BPAP), proportional positive airway pressure support (PPAP), forced oscillation technique, and/or other types of pressure support therapy.

CPAP supplies a fixed positive pressure to maintain a continuous level of positive airway pressure in a patient. BPAP provides a first inspiratory pressure (IPAP) and a second, typically lower, expiratory pressure (EPAP) for easier exhalation during ventilation. In some therapy modes (e.g., PPAP), generator control module 111 may control pressure generator 14 to apply variable pressure support in which the amount of pressure delivered to the patient during inhalation and/or during exhalation is determined and delivered on a breath-by-breath basis. In some embodiments, generator control module 111 may be configured to control pressure generator 14 to temporarily drop the supplied pressure during exhalation (C-Flex) to reduce exhalation effort required by the patent.

In some embodiments, generator control module 111 is configured to control pressure generator 14 to deliver staged pressure support. In staged pressure support therapy, the pressure delivered by pressure generator 14 gradually increases over time. In some embodiments, generator control module 111 may control pressure generator 14 to switch therapy modes based on information related to the respiration of subject 12 and/or other information. For example, generator control module 111 may control pressure generator 111 to change from BPAP to CPAP after a certain number of breaths by subject 12.

Generator control module 111 is configured to control pressure generator 14 based on information related to the output signals from sensors 18, information determined by parameter module 116, information determined by transition module 114, information entered by a user to user interface 22, and/or other information.

Medicament module 112 is configured to obtain a flow including medicament for inhalation by subject 12. Medicament module 112 is configured to obtain the flow (e.g. of breathable gas) including medicament based on one or more of output signals from sensors 18, the therapy regime, information entered by a user to user interface 22, information related to the flow of breathable gas flowing from pressure generator 14, information related to the flow flowing from a supply, and/or other information. In some embodiments, medicament module 112 may be configured to make determinations based on an algorithm. The algorithm may be determined at manufacture, determined by programming the algorithm into processor 20, determined responsive to information entered by a user via user interface 22 (thus allowing user(s) to titrate the composition of gas delivered to subject 12), determined directly based the one or more output signals generated by one or more sensors 18, determined based on previous respiration by subject 12, and/or determined by another method. In some embodiments, medicament module 112 is configured to obtain a flow of a particular volume and/or a flow rate for one or more breaths in a series of consecutive inhalations.

In some embodiments, system 10 includes a module configured to obtain a flow of blending gas for inhalation by subject 12 based on one or more of output signals from sensors 18, the therapy regime, information entered by a user to user interface 22, information related to the flow of breathable gas flowing from pressure generator 14, information related to the flow flowing from a supply (e.g. through blending gas inlet port 17), and/or other information.

Valve control module 113 is configured to control one or more valves 19 to open and close to release one or more flows for inhalation by subject 12, including releasing the flow including medicament into the generated pressurized flow of breathable gas. Valve control module 113 may be configured, responsive to a determination by respiratory phase transition module 114 that subject 12 has started inhaling, to open and close one or more valves 19 to release the obtained flow of breathable gas for an inhalation.

Valve control module 113 is configured to control one or more valves 19 based on information related to the output signals from sensors 18, information determined by parameter module 116, information determined by transition module 114, information determined by recovery quantification module 115, information determined by control module 111, information obtained by medicament module 112, information entered by a user to user interface 22, and/or other information.

Recovery quantification module 115 is configured to determine whether respiration by subject 12 indicates that subject 12 can effectively process medicament. At the onset of dyspnea and/or during the occurrence of related symptoms, subject 12 may not be able to breathe slowly and/or deeply. Some types of medicament (e.g. for dyspnea) may be more efficient and/or effective once a patient is able to breathe slowly and/or deeply. Responsive to an occurrence of dyspnea, system 10 provides relief and/or recovery through pressure support therapy. In some embodiments, such pressure support therapy may be augmented by including a flow of blending gas, for example gas that is enriched with oxygen. Based on output signals from sensors 18 and/or information from one or more computer program modules, recovery quantification module 115 may be configured to determine the current level, type, and/or severity of (the symptoms of) dyspnea. For example, such a determination may be based on one or more breathing parameters related to the respiration of subject 12. By comparing multiple such determinations over a predetermined period, recovery quantification module 115 may determine whether (the symptoms of) dyspnea have subsided sufficiently such that subject 12 can effectively and/or efficiently process medicament. In some embodiments, recovery quantification module 115 may be configured to determine what type of dyspnea is currently occurring, and may respond appropriately based on such a determination. The predetermined period of time may include one or more of one or more respiratory cycles, a period of about 10 seconds, about 30 seconds, about a minute, about 2 minutes, and/or about another period of time, and/or any combination thereof.

Responsive to a determination by the recovery quantification module 115 that respiration by subject 12 indicates that subject 12 can effectively process medicament, subject 12 may be notified, e.g. through user interface 22, that subject 12 may now cause, e.g. through user interface 22, the release of a flow of breathable gas including medicament for inhalation by subject 12. In some embodiments, the transition between the provision of pressure support therapy (that does not include medicament) and respiratory therapy that does include medicament may occur automatically under control of recovery quantification module 115. For example, recovery quantification module 115 may cause and/or initiate valve control module 113 to control one or more valves 19 in order to release the flow of medicament, e.g. into the pressurized flow of breathable gas being delivered to subject 12. In some embodiments, the release of medicament may be augmented by including a flow of blending gas, for example gas that is enriched with oxygen.

In some embodiments, one or more of pressure support therapy, the provision of medicament, and/or the provision of a flow of blending gas may occur simultaneously and/or in any predetermined sequence. For example, pressure support therapy may be followed by the provision of a flow of blending gas that is enriched with oxygen, which may in turn be followed by the provision of (a flow including) medicament. The particular predetermined sequence may depend on and/or be based on output signals from sensors 18, gas and/or breathing parameters, and/or information from one or more computer program modules, and/or other information. For example, operational settings that control such a sequence may be adjusted and/or determined based on information from recovery quantification module 115.

User interface 22 is configured to provide an interface between system 10 and subject 12 and/or other users through which subject 12 and/or other users may provide information to and receive information from system 10. Other users may comprise, for example, a caregiver, a doctor, and/or other users. This enables data, cues, results, and/or instructions and any other communicable items, collectively referred to as "information," to be communicated between a user (e.g., subject 12) and one or more of pressure generator 14, processor 20, and/or other components of system 10. For example, a user may specify one or more therapy regimes that are to be delivered to subject 12 using user interface 22. Generator control module 111 may then customize the therapy regime delivered to the subject based on the one or more inputs made by the user to the user interface. A user may specify a medicament dosage to be delivered to subject 12. Medicament module 112 and/or valve control module 113 may then customize and/or control the dose delivered to the subject based on the one or more inputs made by the user to the user interface. As another example, an accumulated dose, therapy pressures, the breath rate of subject 12, the portable power source energy level, and/or other information may be displayed to a user (e.g., subject 12) via user interface 22.

Examples of interface devices suitable for inclusion in user interface 22 comprise a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 22 comprises a plurality of separate interfaces. In one embodiment, user interface 22 comprises at least one interface that is provided integrally with housing 28.

It is to be understood that other communication techniques, either hard-wired or wireless, are also contemplated by the present disclosure as user interface 22. For example, the present disclosure contemplates that user interface 22 may be integrated with a removable storage interface provided by electronic storage 24. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 22 comprise, but are not limited to, an RS-232 port, RF link, an IR link, modem (telephone, cable, and/or other). In short, any technique for communicating information with system 10 is contemplated by the present disclosure as user interface 22.

In some embodiments, electronic storage 24 comprises electronic storage media that electronically stores information. The electronic storage media of electronic storage 24 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 24 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 24 may store software algorithms, information determined by processor 20, information received via user interface 22, and/or other information that enables system 10 to function properly. Electronic storage 24 may be (in whole or in part) a separate component within system 10, or electronic storage 24 may be provided (in whole or in part) integrally with one or more other components of system 10 (e.g., user interface 22, processor 20, etc.).

Information determined by processor 20 and/or stored by electronic storage 24 may comprise information related to respiration of subject 12, compliance, use frequency, blending gas dosage, and/or other information. The information stored by electronic storage 24 may be viewed via user interface 22, by connecting (wired and/or wireless) to a separate computer, and/or other via other methods. The information stored by electronic storage 24 may be used, for example, to adjust settings, to make adjustments to power source 26, used by a doctor to make medical decisions, and/or for other uses.

Portable power source 26 is configured to power pressure generator 14, one or more sensors 18, one or more valves 19, one or more processors 20, user interface 22, electronic storage 24, and/or other components of system 10 in a portable manner. Power source 26 may comprise one or more power sources connected in series and/or in parallel. In some embodiments, power source 26 is rechargeable. Power source 26 may be recharged via a home AC power source, a car battery outlet, an airplane power outlet, a USB port, a non-contact charging circuit, and/or other recharging methods. In some embodiments, portable power source 26 may supply up to 10V. In some embodiments, portable power source 26 may supply up to 15V. In some embodiments, portable power source may supply up to 20V. Examples of portable power sources that may be included as portable power source 26 include one or more DC batteries, lithium ion cells, lithium polymer cells, nickel metal hydride, and/or other portable power sources. In some embodiments, portable power source 26 is configured to power system 10 upwards of 10 hours of use. In some embodiments, portable power source 26 is configured to power system 10 for up to 10 hours of use. In some embodiments, portable power source 26 is configured to power system 10 for up to 8 hours of use. In some embodiments, portable power source 26 is configured to power system 10 for up to 6 hours of use.

Housing 28 is configured to contain pressure generator 14, subject interface 16, blending gas inlet port 17, medicament inlet port 21, one or more sensors 18, one or more valves 19, one or more processors 20, user interface 22, electronic storage 24, power source 26, flow path 60, exhaust port 62, handle 30, and/or other components of system 10. Housing 28 is configured to contain the components of system 10 in a space small enough to be handheld and portable so pressure support therapy may be delivered at any time during the normal daily activities of subject 12. In some embodiments, the weight of system 10 is up to three pounds. In some embodiments, the weight of system 10 is up to two pounds. In some embodiments, the weight of system 10 is up to one pound. In some embodiments, the volume of housing 28 is up to 135 cubic inches. In some embodiments, the volume of housing 28 is up to 100 cubic inches. In some embodiments, the volume of housing 28 is up to 60 cubic inches.

Flow path 60 is configured to place subject interface 16 in fluid communication with pressure generator 14, one or more valves 19, and/or exhaust port 62. Exhaust port 62 is configured to direct exhaled gas from flow path 60 and/or pressure generator 14 to the ambient atmosphere. In some embodiments, flow through exhaust port 62 may be controlled by a valve 63. Valve 63 may be controlled by processor 20 to close during inhalation of subject 12 and open during exhalation. By way of a non-limiting example, valve control module 113 may control valve 63 to open and/or close based on one or more parameters determined by parameter module 116, information determined by transition module 114, and/or other information. In some embodiments, housing 28 may contain one or more additional ports (e.g., USB) configured to provide a connection point so that portable power source 26 may be recharged, electronic storage 24 may be accessed, and/or for other purposes.

Handle 30 is configured to be attached to and/or formed by housing 28. Handle 30 is configured to be grasped by subject 12 to hold the housing in position with respect to the airway of subject 12 as the pressurized blending gas enriched flow of breathable gas is delivered to the airway of subject 12. Handle 30 may be attached to housing 28 by coupling handle 30 to housing 28 at one or more locations with screws and/or another method of fixing handle 30 to housing 28. Handle 30 may be formed in housing 28 by way of a ridged, knurled, and/or other textured surface. Handle 30 formed in housing 28 may comprise finger shaped surface depressions in housing 28 such that a user's fingers may fit into the finger depressions for gripping system 10. The method for mounting, and/or the form factor for handle 30 formed by housing 28 as described herein are not intended to be limiting. Handle 30 may be attached to and/or formed in housing 28 by any method, in any shape, and/or in any location(s) that allows it to function as described herein.

Figure 2:
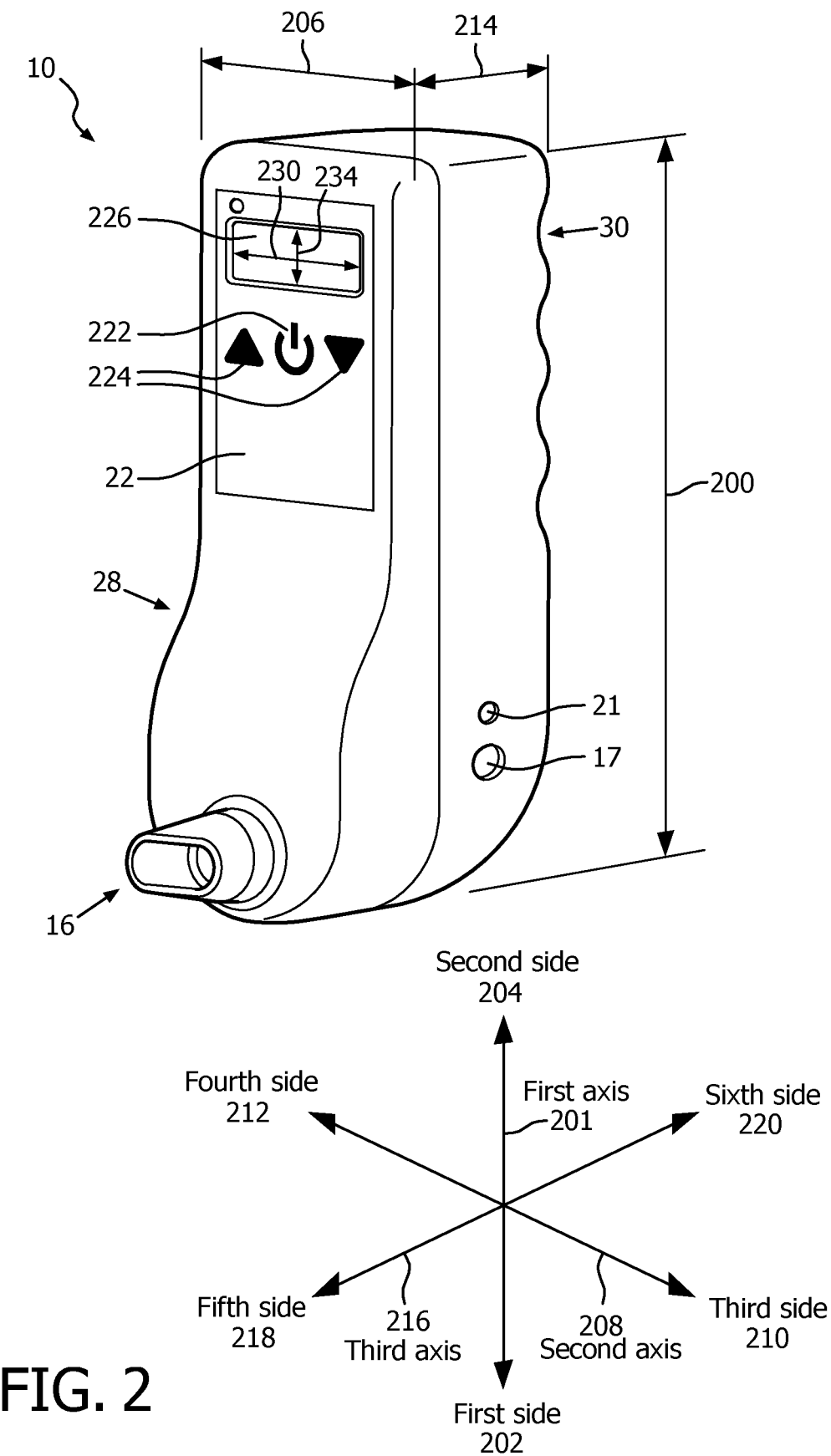
FIG. 2 illustrates an exemplary embodiment of the portable handheld pressure support system.

By way of a non-limiting example, FIG. 2 illustrates a perspective view of an exemplary embodiment of system 10. In this embodiment, housing 28 has a length 200 running along a first axis 201 from a first side 202 to a second side 204 of less than about 7 inches. Length 200 may be between about 5 inches and about 7 inches. Length 200 may be about 6 inches. In some embodiments, housing 28 may have a width 206 running along a second axis 208 from a third side 210 to a fourth side 212 of greater than about 3 inches. Width 206 may be between about 2 inches and about 3 inches. Width 206 may be about 2.5 inches. Housing 28 has a thickness 214 running along a third axis 216 from a fifth side 218 toward a sixth side 220 of less than about 5 inches. Thickness 214 may be between about 4 inches and about 5 inches. Thickness 214 may be about 4.5 inches. The generally rectangular shape and approximate dimensions of housing 28 shown in FIG. 2 are not intended to be limiting. Housing 28 may take any shape that allows it to function as described in the present disclosure.

At least part of user interface 22 is also shown in FIG. 2. In example FIG. 2, user interface 22 is located on fifth side 218 and includes a power button 222, adjustment buttons 224, and a display 226. In this embodiment, display 226 has a width 230 running along second axis 208 from third side 210 to fourth side 212 of greater than about 2 inches. Width 230 may be between about 1 inch and about 2 inches. Width 230 may be about 1.8 inches. Display 226 has a height 234 running along first axis 201 from first side 202 toward second side 204 of greater than about 0.5 inches. Height 234 may be between about 0.5 inches and about 1 inch. Height 234 may be about 0.6 inches.

Examples of subject interface 16, handle 30, medicament inlet port 21, and blending gas inlet port 17 are also shown in FIG. 2. In FIG. 2, handle 30 is formed in housing 28 on sixth side 220 toward second side 204, opposite user interface 22. Subject interface 16 is located on fifth side 218 (the same side as user interface 22) toward first side 202. Subject interface 16 is located in an area where thickness 214 increases along third axis toward fifth side 218 near first side 202. As depicted in FIG. 2, blending gas inlet port 17 and medicament inlet port 21 are located on third side 210 near first side 202. In some embodiments, inlet ports may have a shape other than circular.

The general shapes, locations, and/or approximate dimensions of user interface 22, subject interface 16, handle 30, medicament inlet port 21, and/or blending gas inlet port 17 shown in FIG. 2 and described herein are not intended to be limiting. The features described above may be arranged in any way that allows them to function as described in the present disclosure.

Figure 3:
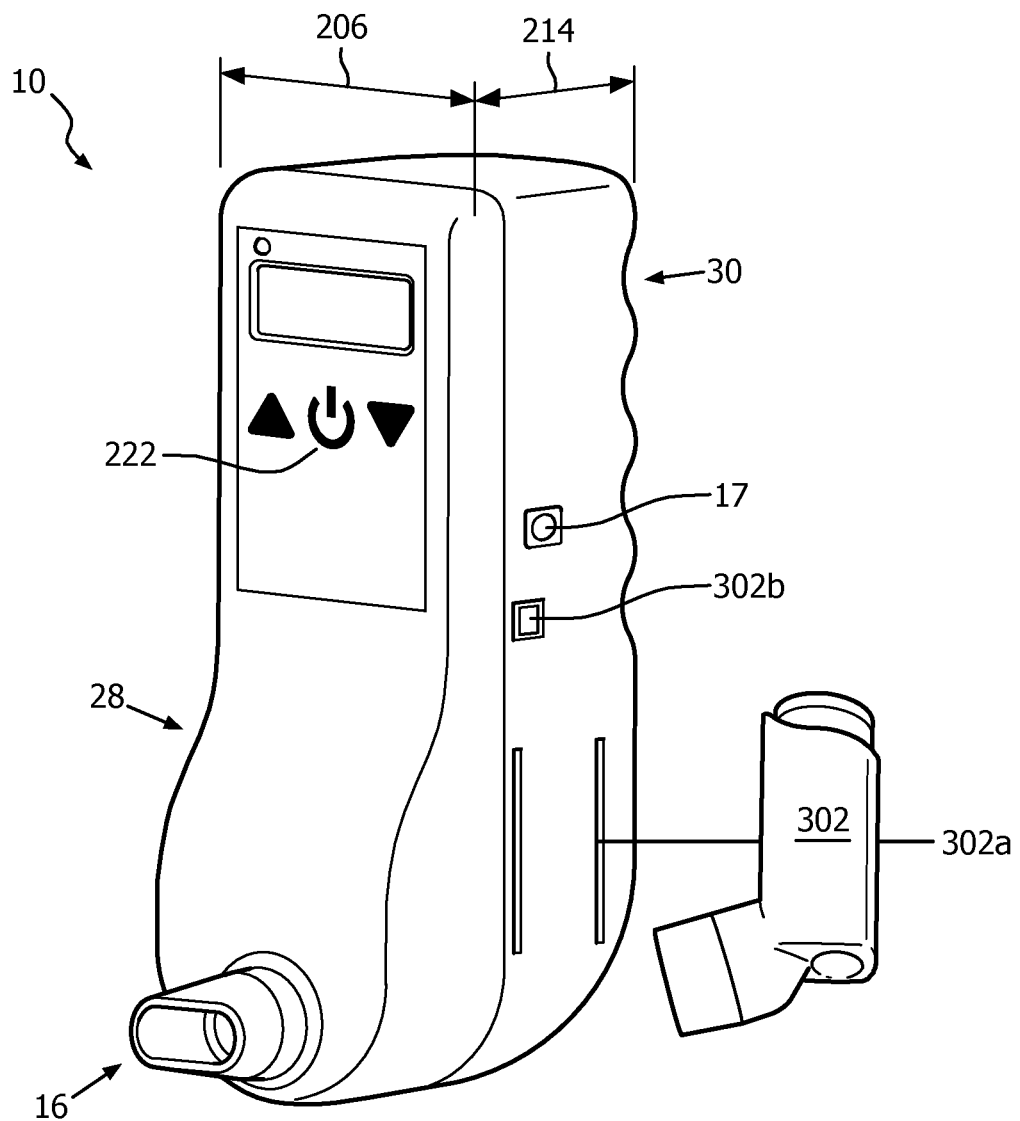
FIG. 3 illustrates an exemplary embodiment of the portable handheld pressure support system removably coupled to a supply of blending gas.

FIG. 3 illustrates system 10 coupled to a source of medicament. The medicament may be held in a metered dose inhaler (MDI) 302. MDI 302 may be removably coupled to medicament inlet port 21 and/or system 10 via an MDI holder 302a. MDI 302 may be manually, automatically and/or programmatically activated through MDI activator 302b. The relative size of medicament source is similar to or smaller than that of system 10. MDI 302 may be configured to be portable with system 10. Coupling may comprise a removable attachment. In some embodiments, coupling may be accomplished through plumbing and/or additional manufactured parts to couple with housing 28. In some embodiments, the source of medicament may be contained in, for example, a canister, an inhaler containing aerosolized medication, a metered dose inhaler (MDI), nebulizer, and/or other portable container separate from system 10. In these embodiments, the containers may be portable, rechargeable, and/or replaceable. The general shape and/or coupling location of MDI 302 shown in FIG. 3 and described herein are not intended to be limiting. The features described above may be arranged in any way that allows them to function as described in the present disclosure.

Figure 4:
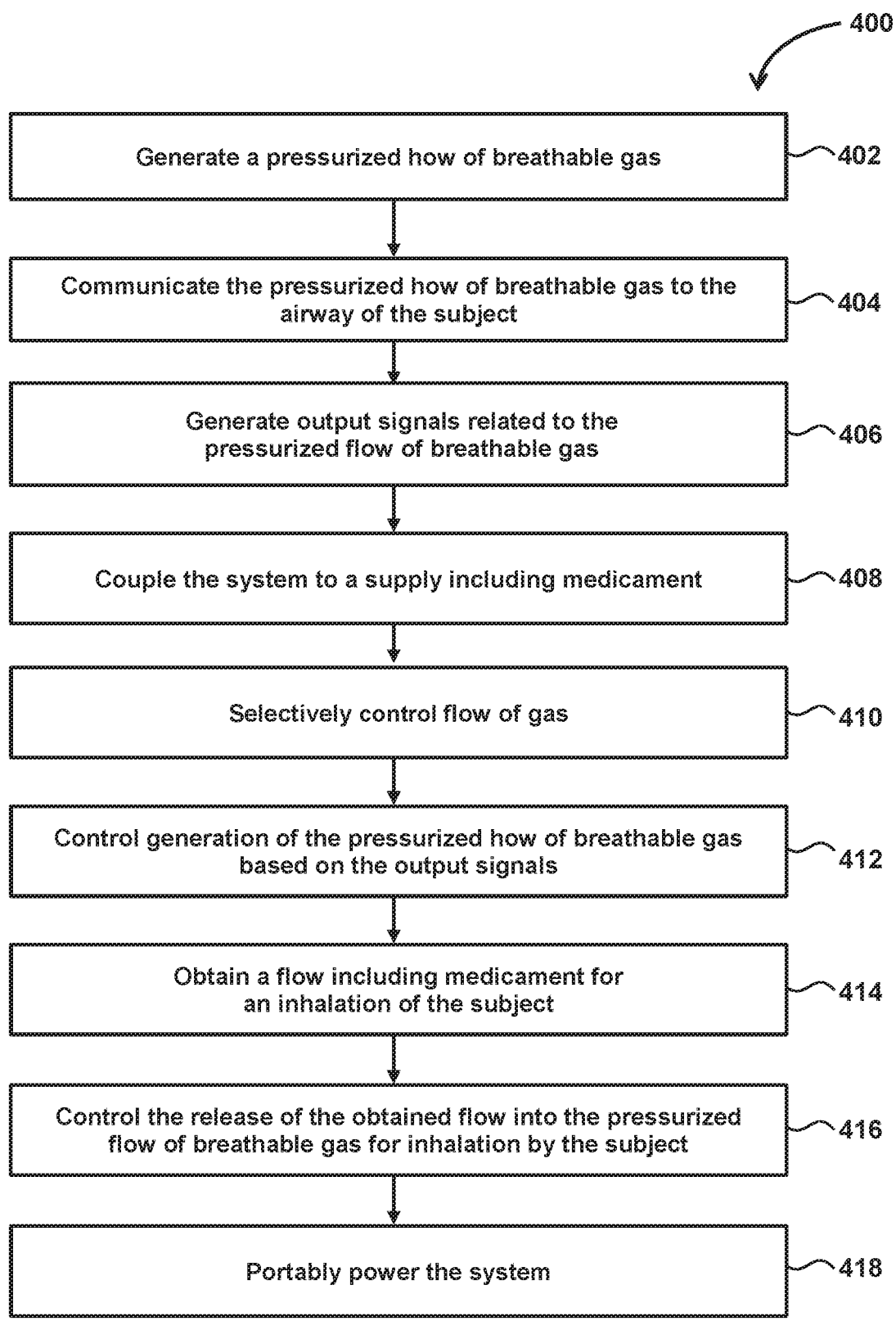
FIG. 4 illustrates a method of providing relief and/or recovery from dyspnea.

FIG. 4 illustrates a method 400 of delivering a blending gas enriched pressurized flow of breathable gas to the airway of a subject with a handheld pressure support system that includes a housing. The housing contains a pressure generator, a subject interface, one or more sensors, a medicament inlet port, a blending gas inlet port, one or more valves, one or more processors, and a power source. The housing forms and/or is attached to a handle. The operations of method 400 presented below are intended to be illustrative. In some embodiments, method 400 may be accomplished with one or more additional operations not described, and/or without one or more of the operations discussed. Additionally, the order in which the operations of method 400 are illustrated in FIG. 4 and described below is not intended to be limiting.

In some embodiments, method 400 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 400 in response to instructions stored electronically on an electronic storage medium. The one or more processing devices may include one or more devices configured through hardware, firmware, and/or software to be specifically designed for execution of one or more of the operations of method 400.

At an operation 402, a pressurized flow of breathable gas is generated with the pressure generator. In some embodiments, operation 402 is performed by a pressure generator the same as or similar to pressure generator 14 (shown in FIG. 1 and described herein).

At an operation 404, the pressurized flow of breathable gas is communicated to an airway of the subject with the subject interface. In some embodiments, operation 404 is performed by a subject interface the same as or similar to subject interface 16 (shown in FIG. 1 and described herein).

At an operation 406, one or more output signals conveying information related to one or more gas parameters of the pressurized flow of breathable gas are generated with the one or more sensors. In some embodiments, operation 406 is performed by sensors the same as or similar to sensors 18 (shown in FIG. 1 and described herein.)

At an operation 408, a supply including medicament is coupled the housing with the medicament inlet port. In some embodiments, operation 408 is performed by an inlet port the same as or similar to medicament inlet port 21 (shown in FIG. 1 and described herein).

At an operation 410, a flow of gas is selectively controlled with one or more valves. In some embodiments, operation 410 is performed by a valve the same as or similar to one or more valves 19 (shown in FIG. 1 and described herein).

At an operation 412, the generation of the pressurized flow of breathable gas is controlled based on the output signals, according to a positive pressure support therapy regime. In some embodiments, operation 412 is performed by a processor module the same as or similar to generator control module 111 (shown in FIG. 1 and described herein).

At an operation 414, a flow including medicament is obtained for an inhalation of the subject. In some embodiments, operation 414 is performed by a processor module the same as or similar to medicament module 112 (shown in FIG. 1 and described herein).

At an operation 416, the one or more valves are controlled to release the obtained flow including medicament into the pressurized flow of breathable gas for inhalation by the subject. In some embodiments, operation 416 is performed by a processor module the same as or similar to valve control module 113 (shown in FIG. 1 and described herein).

At an operation 418, the pressure generator, the one or more sensors, the one or more valves, and the one or more processors are powered with the portable power source. In some embodiments, operation 418 is performed by a portable power source the same as or similar to power source 26 (shown in FIG. 1 and described herein.)

The present invention further contemplates that portable handheld pressure support system 10 includes one or more additional sensors 500 (see FIG. 1) adapted to measure movement, motion, and/or acceleration of the device. For example, accelerometer 500 can be used to measure the amount of steps taken or activity performed by the user. Such information is valuable in providing an indication of how active the patient is. The accelerometer can also be used to monitor the number of uses of the device, which would indicate compliance to the use of device. Thus, the contemplated device has the added functionality or being able to monitor user activity and compliance to a prescribed drug delivery treatment and/or use of device in treating dyspneas.

In an exemplary embodiment, accelerometer 500 provides an output to one or more processors 20, which use this information to identify and count the number of times the device is used, which could measure the activity of the patient with the device, the drug being delivered to the patient. The present invention further contemplates providing this usage information to an exacerbation detection algorithms, either via a telecommunication or to such algorithms contained in the device. The exacerbation detection algorithms to determine whether the patient is experience an exacerbation of increase in their symptoms. That information is can be given to the user via the user interface and/or be used to provide a warning or other instructions, for example, that the user seek medical attention if.

In short, the addition of motion/acceleration detecting capabilities allows device 10 to indicate the stability and health of the patient. The usage of the device and drug through the device allows for compliance monitoring of COPD patients. This device could be used in conjunction with telemonitoring for COPD readmission and exacerbation detection. It can also be used to track the activity of the patient and provide data statistics regarding, for example, increases in activity as compared to the number of times they use the device. It will also act as a tool for monitoring oxygen therapy data usage as compared to activity.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A portable handheld pressure support system configured to provide recovery from dyspnea of a subject, without needing to be worn by the subject, the pressure support system comprising:
   a pressure generator configured to generate a pressurized flow of breathable gas for delivery to an airway of the subject;
   a subject interface configured to communicate the pressurized flow of breathable gas to the airway of the subject;
   a medicament inlet port configured to couple to a supply that includes medicament;
   one or more valves configured to selectively control a flow including medicament through the medicament inlet port;
   one or more sensors configured to generate output signals conveying information related to one or more gas parameters of the pressurized flow of breathable gas and one or more flow parameters of the flow including medicament flowing through the medicament inlet port;
   one or more processors configured to execute computer program modules, the computer program modules comprising:

a generator control module configured to control operation of the pressure generator to generate the pressurized flow of breathable gas based on the output signals from the one or more sensors, in accordance with a positive pressure support therapy regime, a medicament module configured to obtain a flow including medicament for inhalation by the subject, and a valve control module configured to control the one or more valves in order to release the obtained flow including medicament into the pressurized flow of breathable gas for inhalation by the subject based on the output signals, from the one or more sensors, conveying the information related to the one or more gas parameters of the pressurized flow of breathable gas and the one or more flow parameters of the flow including medicament flowing through the medicament inlet port;

a portable power source configured to power the pressure generator, the one or more sensors, the one or more valves, and the one or more processors;

a housing configured to contain the pressure generator, the subject interface, the one or more sensors, the medicament inlet port, the one or more valves, the one or more processors, and the power source; and a handle attached to and/or formed by the housing configured to be grasped by a hand of the subject to hold the housing such that the subject interface is carried with the housing into position with respect to the airway of the subject as the pressurized flow of breathable gas is delivered to the airway of the subject.

2. The system of claim 1, wherein the maximum volume of the housing is 135 cubic inches.

3. The system of claim 1, wherein the computer program modules further comprise:

a respiratory phase transition module configured to determine the start of inhalation for a respiratory cycle of the subject, wherein the determination made by the respiratory phase transition module are based on the output signals, wherein the valve control module is further configured, responsive to a determination by the respiratory phase transition module that the subject has started an inhalation, to control the one or more valves in order to release the obtained flow including medicament into the pressurized flow of breathable gas for inhalation by the subject.

4. The system of claim 1, wherein the computer program modules further comprises: a recovery quantification module configured to determine whether respiration by the subject indicates that the subject can effectively process the medicament, wherein the valve control module is further configured to initiate the release of the obtained flow including medicament into the pressurized flow of breathable gas based on a determination by the recovery quantification module.

5. The system of claim 1, further comprising:

a blending gas inlet port configured to obtain a flow of blending gas for inhalation by the subject, wherein the one or more sensors are further configured to generate the output signals conveying information related to one or more gas parameters of the flow of blending gas flowing through blending gas inlet port, wherein the one or more valves are further configured to selectively control the flow of blending gas through the blending gas inlet port, and wherein the valve control module is further configured to control the one or more valves in order to release the obtained flow of blending gas into the pressurized flow of breathable gas for inhalation by the subject based on the output signals from the one or more sensors.

6. A method of controlling and operating a handheld pressure support system that includes a housing that includes a pressure generator, a subject interface, one or more sensors, a medicament inlet port, one or more valves, one or more processors, the housing forming and/or being attached to a handle, and a power source, the method comprising:

generating a pressurized flow of breathable gas by the pressure generator;

communicating the pressurized flow of breathable gas to an airway of a subject with the subject interface;

coupling, by the medicament inlet port, the housing to a supply that includes medicament;

generating output signals conveying information related to one or more gas parameters of the pressurized flow of breathable gas and one or more flow parameters of a flow including medicament flowing through the medicament inlet port by the one or more sensors;

selectively controlling, by the one or more valves, the flow including medicament through the medicament inlet port;

controlling generation of the pressurized flow of breathable gas based on the output signals from the one or more sensors, in accordance with a positive pressure support therapy regime;

obtaining the flow including medicament for inhalation by the subject;

controlling the one or more valves in order to release the obtained flow of medicament into the pressurized flow of breathable gas for inhalation by the subject based on the output signals, from the one or more sensors, conveying the information related to the one or more gas parameters of the pressurized flow of breathable gas and the one or more flow parameters of the flow including medicament flowing through the medicament inlet port;

portably powering, by the power source, the pressure generator, the one or more sensors, the one or more valves, and the one or more processors;

grasping by a hand of the subject, the handle to hold the housing such that the subject interface is carried with the housing into position with respect to the airway of the subject as the pressurized flow of breathable gas is delivered to the airway of the subject.

7. The method of claim 6, wherein a maximum volume of the housing is 135 cubic inches.

8. The method of claim 6, further comprising:

determining the start of inhalation and/or the start of exhalation for a respiratory cycle of the subject based on the output signals, and wherein controlling the one or more valves in order to release the obtained flow of medicament is responsive to a determination for the respiratory cycle of the subject.

9. The method of claim 6, further comprising:

obtaining an effectiveness determination whether respiration by the subject indicates that the subject can effectively process the medicament, wherein controlling the one or more valves in order to release the obtained flow of medicament is based on the effectiveness determination.

10. The method of claim 6, wherein the housing further includes a blending gas inlet port, the method further comprising:

coupling, by the blending gas inlet port, the housing to a supply of blending gas;

selectively controlling, by the one or more valves, a flow of blending gas through the blending gas inlet port;

obtaining the flow of blending gas for inhalation by the subject;

generating the output signals conveying information related to one or more gas parameters of the flow of blending gas flowing through the blending gas inlet port by the one or more sensors; and controlling the one or more valves in order to release the obtained flow of blending gas into the pressurized flow of breathable gas for inhalation by the subject based on the output signals from the one or more sensors.

11. A portable handheld pressure support system configured to provide recovery from dyspnea of a subject, without needing to be worn by the subject, the system comprising:

generating means for generating a pressurized flow of breathable gas;

means for communicating the pressurized flow of breathable gas to the airway of the subject;

coupling means for coupling to a supply including medicament;

first means for selectively controlling a flow including medicament through the coupling means;

sensing means for generating output signals conveying information related to one or more gas parameters of the pressurized flow of breathable gas and one or more flow parameters of the flow including medicament flowing through the coupling means;

means for controlling the generating means based on the output signals from the sensing means, in accordance with a positive pressure support therapy regime;

control means for controlling the first means based on the output signals, from the sensing means, conveying the information related to the one or more gas parameters of the pressurized flow of breathable gas and the one or more flow parameters of the flow including medicament flowing through the medicament inlet port in order to release the obtained flow including medicament into the pressurized flow of breathable gas for inhalation by the subject;

power means for portably powering the generating means, the sensing means, and the first means;

housing means for containing the generating means, the sensing means, the first means, and the power means; and means for engaging a hand of the subject to be grasped by the subject, the means for engaging being configured to be grasped by the hand of the subject to hold the housing means such that the means for communicating is carried with the housing means for containing into position with respect to the airway of the subject, the means for engaging being connected to and/or formed by the housing means.

12. The system of claim 11, wherein a maximum volume of the housing means is 135 cubic inches.

13. The system of claim 11, further comprising:

means for determining the start of inhalation and/or the start of exhalation for a respiratory cycle of the subject based on the output signals, and wherein operation of the control means is responsive to a determination for the respiratory cycle of the subject.

14. The system of claim 11, further comprising: means for obtaining an effectiveness determination whether respiration by the subject indicates that the subject can effectively process the medicament, wherein operation of the control means is based on the effectiveness determination.

15. The system of claim 11, further comprising: means for coupling to a supply of blending gas;

wherein the first means is further for selectively controlling a flow of blending gas through the means for coupling to a supply of blending gas, means for obtaining the flow of blending gas for inhalation by the subject;

wherein the sensing means is further for generating the output signals conveying information related to one or more gas parameters of the flow of the blending gas; and wherein the control means is further for controlling the first means in order to release the obtained flow of blending gas into the pressurized flow of breathable gas for inhalation by the subject based on the output signals from the sensing means.

* * * * *